(12) United States Patent
Dolan et al.

(10) Patent No.: US 9,058,354 B2
(45) Date of Patent: Jun. 16, 2015

(54) INTEGRATED MULTI-CRITERIA DECISION SUPPORT FRAMEWORK

(71) Applicant: University of Rochester, Rochester, NY (US)

(72) Inventors: James Dolan, Webster, NY (US); Peter Veazie, Rochester, NY (US)

(73) Assignee: University of Rochester, Rochester, NY (US)

( * ) Notice: Subject to any disclaimer, the term of this patent is extended or adjusted under 35 U.S.C. 154(b) by 96 days.

(21) Appl. No.: 13/750,922

(22) Filed: Jan. 25, 2013

(65) Prior Publication Data

US 2013/0198207 A1   Aug. 1, 2013

Related U.S. Application Data

(60) Provisional application No. 61/591,257, filed on Jan. 26, 2012.

(51) Int. Cl.
*G06F 17/30* (2006.01)
*G06F 19/00* (2011.01)
*G06Q 50/22* (2012.01)

(52) U.S. Cl.
CPC ........ *G06F 17/30424* (2013.01); *G06F 19/345* (2013.01); *G06Q 50/22* (2013.01)

(58) Field of Classification Search
CPC .. G06F 17/30424; G06F 19/345; G06Q 50/22
USPC ........................................................ 707/749
See application file for complete search history.

(56) References Cited

U.S. PATENT DOCUMENTS

| 5,774,121 | A | * | 6/1998 | Stiegler ......................... 715/769 |
| 5,908,383 | A | * | 6/1999 | Brynjestad .................... 600/300 |
| 6,120,440 | A | * | 9/2000 | Goknar .......................... 600/300 |
| 6,260,033 | B1 | * | 7/2001 | Tatsuoka ......................... 706/45 |
| 7,080,071 | B2 | * | 7/2006 | Henrion et al. ............... 707/713 |

(Continued)

FOREIGN PATENT DOCUMENTS

| JP | 2013-93019 | * | 5/2013 | ............. G06Q 50/22 |
| WO | WO 97/50046 | * | 12/1997 | ............. G06F 17/00 |
| WO | WO 2012/122198 A1 | * | 9/2012 | ............. G06F 19/00 |

OTHER PUBLICATIONS

Dolan, James G., "Multi-Criteria Clinical Decision Support—A Primer on the Use of Multiple-Criteria Decision-Making Methods to Promote Evidence-Based, Patient-Centered Healthcare", Patient 2010, 3(4): pp. 229-248, 2010.*

(Continued)

*Primary Examiner* — Phuong Thao Cao
(74) *Attorney, Agent, or Firm* — James W. Hill; McDermott Will & Emery LLP

(57) ABSTRACT

Integrated multi-criteria decision frameworks disclosed herein can facilitate making good decisions when faced with a complex choice among several alternatives with different combinations of strengths and weaknesses. Some decision support systems using multi-criteria methods can combine multiple multi-criteria methods in a single adaptable decision support intervention. In some embodiments, the framework can include some or all of the following modules: a decision strategy module; a balance sheet module; an interactive decision dashboard module; an ordinal ranking module; a direct weighting module; and an Analytic Hierarchy Process (AHP) module.

20 Claims, 14 Drawing Sheets

(56) References Cited

U.S. PATENT DOCUMENTS

| | | | | |
|---|---|---|---|---|
| 7,213,009 | B2* | 5/2007 | Pestotnik et al. | 706/46 |
| 7,496,518 | B1* | 2/2009 | Cayton et al. | 705/321 |
| 7,553,834 | B2* | 6/2009 | Metzner | 514/212.05 |
| 7,930,189 | B2* | 4/2011 | Kuo | 705/2 |
| 8,152,523 | B2* | 4/2012 | Sporbert et al. | 433/24 |
| 8,548,937 | B2* | 10/2013 | Saigal et al. | 706/52 |
| 8,676,607 | B2* | 3/2014 | Patel et al. | 705/3 |
| 8,706,521 | B2* | 4/2014 | Ramarajan et al. | 705/2 |
| 8,762,177 | B2* | 6/2014 | Dahan | 705/3 |
| 2002/0077931 | A1* | 6/2002 | Henrion et al. | 705/26 |
| 2002/0095316 | A1* | 7/2002 | Toan et al. | 705/4 |
| 2003/0046113 | A1* | 3/2003 | Johnson et al. | 705/3 |
| 2004/0260666 | A1* | 12/2004 | Pestotnik et al. | 706/46 |
| 2005/0021240 | A1* | 1/2005 | Berlin et al. | 702/20 |
| 2005/0144042 | A1* | 6/2005 | Joffe et al. | 705/2 |
| 2005/0203773 | A1* | 9/2005 | Soto et al. | 705/2 |
| 2005/0271996 | A1* | 12/2005 | Sporbert et al. | 433/24 |
| 2006/0111933 | A1* | 5/2006 | Wheeler | 705/2 |
| 2006/0136142 | A1* | 6/2006 | Berlin et al. | 702/20 |
| 2006/0241972 | A1* | 10/2006 | Lang et al. | 705/2 |
| 2007/0033060 | A1* | 2/2007 | Gopalan et al. | 705/1 |
| 2007/0055544 | A1* | 3/2007 | Jung et al. | 705/2 |
| 2007/0168227 | A1* | 7/2007 | Fleming et al. | 705/2 |
| 2007/0198296 | A1* | 8/2007 | Pellinat et al. | 705/2 |
| 2007/0198401 | A1* | 8/2007 | Kunz | 705/38 |
| 2007/0219995 | A1* | 9/2007 | Heumann et al. | 707/7 |
| 2008/0172214 | A1* | 7/2008 | Col et al. | 703/11 |
| 2008/0288023 | A1* | 11/2008 | John | 607/59 |
| 2008/0319822 | A1* | 12/2008 | LaJoie et al. | 705/9 |
| 2009/0094060 | A1* | 4/2009 | Johnson et al. | 705/3 |
| 2010/0106518 | A1* | 4/2010 | Kuo | 705/2 |
| 2010/0312076 | A1* | 12/2010 | Bly et al. | 600/301 |
| 2011/0104717 | A1* | 5/2011 | Fantl et al. | 435/7.21 |
| 2011/0125467 | A1* | 5/2011 | Col et al. | 703/2 |
| 2011/0269097 | A1* | 11/2011 | Sporbert et al. | 433/24 |
| 2011/0289077 | A1* | 11/2011 | Wade et al. | 707/723 |
| 2012/0016690 | A1* | 1/2012 | Ramarajan et al. | 705/2 |
| 2012/0047105 | A1* | 2/2012 | Saigal et al. | 706/52 |
| 2012/0084064 | A1* | 4/2012 | Dzenis et al. | 703/11 |
| 2012/0253771 | A1* | 10/2012 | Col et al. | 703/11 |
| 2013/0035253 | A1* | 2/2013 | Rosen et al. | 506/9 |
| 2013/0043991 | A1* | 2/2013 | Hyde et al. | 340/539.1 |
| 2013/0085735 | A1* | 4/2013 | Vilsmeier | 703/11 |
| 2013/0117034 | A2* | 5/2013 | Ghouri et al. | 705/2 |
| 2013/0191159 | A1* | 7/2013 | Camacho et al. | 705/3 |
| 2013/0198207 | A1* | 8/2013 | Dolan et al. | 707/749 |
| 2013/0238364 | A1* | 9/2013 | Glotko | 705/3 |
| 2013/0268290 | A1* | 10/2013 | Jackson et al. | 705/2 |
| 2014/0039929 | A1* | 2/2014 | Vdovjak et al. | 705/3 |
| 2014/0072939 | A1* | 3/2014 | Dahan | 434/262 |
| 2014/0081650 | A1* | 3/2014 | Sachs | 705/2 |
| 2014/0088990 | A1* | 3/2014 | Nawana et al. | 705/2 |
| 2014/0122185 | A1* | 5/2014 | Rai et al. | 705/7.36 |
| 2014/0162887 | A1* | 6/2014 | Martin et al. | 506/8 |
| 2014/0199273 | A1* | 7/2014 | Cesano et al. | 424/93.7 |
| 2014/0336743 | A1* | 11/2014 | Zotz | 623/1.11 |

OTHER PUBLICATIONS

Choo et al., "Interpretation of Criteria Weights in Multicriterial Decision Making", In Computer & Industrial Engineering 37 (1999): pp. 527-541, 1999.*

Leighl et al., "Treatment Decision Aids in Advanced Cancer: When the Goal is Not Cure and the Answer is Not Clear", In Journal of Clinical Oncology, vol. 22, No. 9, May 2004, pp. 1759-1762.*

Hofmann et al., "Visual Aids for Multimodal Treatment Options to Support Decision Making of Patients with Colorectal Cancer", BMC Medical Informatics and Decision Making 2012, 12:118, 9 pages.*

O'Connor et al., "Decision Aids for Patients Considering Options Affecting Cancer Outcomes: Evidence of Efficacy and Policy Implications", In Journal of the National Cancer Institute Monographs No. 25, 1999, pp. 67-80.*

Brundage et al., "A treatment trade-off based decision aid for patients with locally advanced non-small cell lung cancer", Health Expectations, 2000, 3(1): pp. 55-68.*

Kiritsis et al., "Multi-criteria decision aid for product end of life options selection", IEEE International Symposium on Electronics and the Environment, 2003, pp. 48-53.*

Campbell, et al., "Framework for design and evaluation of complex interventions to improve health," BMJ Sep. 16, 2000, vol. 321, pp. 694-696.

Carnes, et al., "Influences on older people's decision making regarding choice of topical or oral NSAIDs for knee pain: qualitative study," BMJ 2008, vol. 336 7 pages.

Chen, "Information visualization," Information Visualization, Jul./Aug. 2010, vol. 2, pp. 387-403.

Fagerlin, et al., "Reducing the influence of anecdotal reasoning on people's health care decisions: is a picture worth a thousand statistics?" Med Decis Making 2005, 25(4):398-405.

Feldman-Stewart, et al., "Challenges for designing and implementing decision aids," Patient Educ Couns 2004, 54(3):265-273.

Feldman-Stewart, et al. "Further Insight into the Perception of Quantitative Information: Judgments of Gist in Treatment Decisions," Med Decis Making 2007, 27(1):34-43.

Feldman-Stewart, et al., "Perception of quantitative information for treatment decisions," Med Decis Making 2000, 20(2):228-238.

Fuller, et al., "Older people's understanding of cumulative risks when provided with annual stroke risk information," Postgrad Med J 2004, 80(949):677-678.

Hibbard, et al., "Supporting informed consumer health care decisions: data presentation approaches that facilitate the use of information in choice," Annual review of public health 2003, 24:413-433.

Légaré, et al., "Barriers and facilitators to implementing shared decision-making in clinical practice: update of a systematic review of health professionals' perceptions," Patient Education and Counseling 2008, 73(3):526-535.

Légaré, et al., "Interventions for improving the adoption of shared decision making by healthcare professionals," Cochrane Database of Systematic Reviews (Online) 2010(5):CD006732-CD006732, 46 pages.

Lipkus, "Numeric, Verbal, and Visual Formats of Conveying Health Risks," Suggested Best Practices and Future Recommendations. Medical Decision Making 2007, 27(5):696-713.

Meyer, et al., "Information structure and the relative efficacy of tables and graphs," Human Factors 1999, 41(4):570-570, pp. 570-587.

Natter, et al., "Effects of active information processing on the understanding of risk information," Appl. Cognit Psychol, Jan. 2005, vol. 19, Issue 1, pp. 123-135.

Nelson, et al., "Rethinking the objectives of decision aids: a call for conceptual clarity," Med Decis Making 2007, 27(5):609-618.

Nelson, et al., "Clinical Implications of Numeracy: Theory and Practice," Annals of Behavioral Medicine 2008, 35(3):261-274.

O'Connor, et al., "Decision aids for people facing health treatment or screening decisions," Cochrane Database Syst Rev 2009(3):CD001431, pp. 1-106.

O'Connor, et al., "Modifying Unwarranted Variations in Health Care: Shared Decision Making Using Patient Decision Aids," Health Affairs, Oct. 7, 2004: doi: 10.1377/hlthaff.var.63, pp. 63-72.

O'Connor, et al., "Toward The 'Tipping Point': Decision Aids and Informed Patient Choice," Health Affairs 2007, 26(3):716-725.

Speier, "The influence of information presentation formats on complex task decision-making performance," International Journal of Human-Computer Studies 2006, 64(11):1115-1131.

Speier, et al. "The influence of query interface design on decision-making performance," Mis Quarterly 2003:397-423.

Svenson, "Differentiation and consolidation theory of human decision making: A frame of reference for the study of pre- and post-decision processes," Acta Psychologica 1992, 80(1-3):143-168.

Vessey, "Cognitive Fit: A Theory-Based Analysis of the Graphs Versus Tables Literature," Decision Sciences 1991, 22(2):219-240.

Waters, et al. "Formats for improving risk communication in medical tradeoff decisions," J Health Commun 2006, 11(2):167-182.

(56) References Cited

OTHER PUBLICATIONS

Whelan, et al., "Effect of a decision aid on knowledge and treatment decision making for breast cancer surgery: a randomized trial," JAMA: The Journal of the American Medical Association 2004, 292(4):435-441.

Whelan, et al., "Helping Patients Make Informed Choices: A Randomized Trial of a Decision Aid for Adjuvant Chemotherapy in Lymph Node-Negative Breast Cancer," J Natl Cancer Inst 2003, 95(8):581-587.

* cited by examiner

|  | Criterion A | Criterion B | Criterion C | Criterion D |
|---|---|---|---|---|
| Alternative 1 | A1 | B1 | C1 | D1 |
| Alternative 2 | A2 | B2 | C2 | D2 |
| Alternative 3 | A3 | B3 | C3 | D3 |

FIG. 3

| Treatment Options | Effectiveness | | Risk of side effects | | Cost |
|---|---|---|---|---|---|
| | Stop disease from getting worse | Control Symptoms | Serious | Minor | Monthly cost to patient |
| | Percent of patients taking the drug who benefit | | | | |
| Drug A | 95% | 65% | 0.1% | 1% | $15 |
| Drug B | 90% | 75% | 0.5% | 5% | $50 |
| Drug C | 85% | 85% | 1% | 10% | $100 |

300

The first step in exploring your options is to rank order the difference among the treatment options based on how important they are to you in making your decision. In the boxes below, please indicate how important you think these differences are.

Your choice of treatment depends on the differences among the options in terms of treatment, effectiveness, risk of side effects and your out-of-pocket expense Which of these differences do you think is most important in making this decision?

○ Effectiveness    ● Side Effects    ○ Cost

Which of these differences do you think is the second most important in making this decision?

● Effectiveness    ○ Side Effects    ○ Cost

Which of these differences do you think is the least important in making this decision?

○ Effectiveness    ○ Side Effects    ● Cost

Effectiveness can be divided into two parts. The first is effectiveness in stopping the disease from getting worse. The other is relieving pain and other symptoms of the disease. In making this decision, which aspect of treatment effectiveness is more important to you?

○ Stopping the disease from getting worse    ● Relieving the symptoms

There are two kinds of potential side effects. The first is serious side effects that in themselves could affect your health permanently. The other is more minor side affects that will resolve completely and result in no permanent damage. In making this decision, which type of side effect is more important?

● Serious side effects    ○ Minor side effects

502

The chart below shows what happens when we combine your preferences with the information we have about the treatment options. The treatment preference score indicates how well each option matches your preferences. Higher scores are preferable to lower ones.

Drug C
Drug B
Drug A 0.00  0.10  0.20  0.30  0.40  0.50  0.60

| Drug | Pain relief * | Risk of side effects | Risk of drug-drug interactions | Cost | Administration |
|---|---|---|---|---|---|
| Acetaminophen | 0.21 | Low | Moderate | Low | 1 tablet every 6 hours |
| Topical NSAID | 0.41 | Low | Low | High | Cream twice a day |
| Capsaicin | 0.30 | Low | Low | Moderate | Cream twice a day |
| NSAID + misoprostol | 0.32 | High | High | Moderate | 2 tablets twice a day |
| NSAID + PPI | 0.32 | Moderate | High | Very High | 2 tablets twice a day |
| NSAIDs | 0.32 | Moderate | High | Low | 1 tablet twice a day |
| Celecoxib | 0.44 | Moderate | High | High | 1 tablet twice a day |
| Chondroitin sulfate | 0.30 | Low | Low | Moderate | 1 tablet twice a day |
| Glucosamine sulfate | 0.45 | Low | Moderate | Moderate | 1 tablet twice a day |

\* – Pain relief summarized using reported effect size.

Abbreviations: NSAID = non-steroidal anti-inflammatory drug; PPI = proton pump inhibitor

FIG. 7

| Variable | Number (percent) |
|---|---|
| Gender | Male: 7 (28%)<br>Female: 18 (72%) |
| Racial/ethnic background | White: 19 (76%)<br>African-American: 2 (8%)<br>Hispanic: 1 (4%)<br>Asian: 3 (12%) |
| Highest Education level | Less than High School: 1 (4%)<br>High School: 2 (8%)<br>Some college, no degree: 3 (12%)<br>Associate's degree: 11 (44%)<br>Bachelor's degree: 4 (16%)<br>Post-graduate training: 4 (16%) |
| Recruitment source | Office staff: 7 (28%)<br>Website volunteer: 8 (32%)<br>Practice volunteer: 6 (24%)<br>Department staff volunteer: 4 (16%) |
| Newest Vital Sign Health Literacy category | Adequate literacy: 18 (72%)<br>Po sible limited literacy: 5 (20%)<br>High likelihood limited literacy: 2 (8%) |
| REALM grade level | High School: 21 (84%)<br>7th - 8th grade: 3 (12%)<br>4th to 6th grade: 1 (4%) |
| | Mean (sd, range) |
| Age, years | 51.4, (13.8, 22 to 71) |
| Subjective numeracy scale | 4 (0.75, 2.25 to 5.38) |

| Category & question | Number of responses | Mean (SD)* | Source |
|---|---|---|---|
| Ease of use, mechanical | | | |
| a. I found the program easy to use | 25 | 6.2 (1.1) | WebQual |
| b. It was easy to find information and move through the program. | 25 | 6.2 (1.2) | WebQual |
| c. The design of the program was appropriate. | 25 | 6.3 (1.0) | WebQual |
| d. I think I could learn to use the program on my own. | 25 | 5.8 (1.8) | UTAT |
| Ease of use, cognitive | | | |
| a. I found the program clear and easy to understand. | 24 | 6.1 (1.1) | WebQual |
| b. The program provides accurate information. | 25 | 6.2 (1.2) | WebQual |
| c. The program provide believable information. | 24 | 5.8 (1.4) | WebQual |
| d. The program provide relevant information. | 24 | 6.1 (1.1) | WebQual |
| e. The program provide easy to understand information. | 24 | 6.3 (1.0) | WebQual |
| f. The program provides information at the right level of detail. | 24 | 6.5 (0.6) | WebQual |
| g. The program provides information in an appropriate format. | 24 | 6.4 (6.5) | WebQual |
| Ease of use, emotional | | | |
| a. I felt nervous using the program. | 24 | 3.1 (2.5) | UTAT |
| b. I would not wish to use the program to help with my medical care because I am afraid I would make mistakes. | 25 | 2.6 (1.7) | UTAT |
| c. The program was intimidating to me. | 25 | 2.4 (1.9) | UTAT |
| Decision-aiding effectiveness | | | |
| a. I would find this program useful in treating my arthritis pain. | 25 | 5.9 (1.7) | UTAT |
| b. Using this program would help me learn about my treatment options more quickly. | 25 | 5.8 (1.3) | UTAT |
| c. Using this program would increase my chance of controlling my arthritis pain safely and effectively. | 25 | 5.8 (1.6) | UTAT |
| d. If I could, I would use this program. | 23 | 6.2 (1.0) | UTAT |

FIG. 9B

| Category & question | Number of responses | Mean (SD)* | Source |
|---|---|---|---|
| Decision-aiding effectiveness | | | |
| a. I would find this program useful in treating my arthritis pain. | 25 | 5.9 (1.7) | UTAT |
| b. Using this program would help me learn about my treatment options quickly. | 25 | 5.8 (1.3) | UTAT |
| c. Using this program would increase my chance of controlling my arthritis pain safely and effectively. | 25 | 5.8 (1.6) | UTAT |
| d. If I could, I would use this program. | 23 | 6.2 (1.0) | UTAT |
| e. I think the program would make it easier for me to talk to my doctor about my arthritis pain treatment. | 23 | 6.2 (1.9) | WebQual |
| f. I feel confident that the program would help me treat my arthritis pain better. | 23 | 5.8 (1.2) | WebQual |
| g. The program would help me get the arthritis treatment that is best for me. | 23 | 5.9 (1.4) | WebQual |
| Decisional conflict scale, Informed sub-scale | | | |
| a. I know what options are available to me for treating my arthritis pain. | 23 | 6.1 (1.3) | |
| b. I know the benefits of each option. | 23 | 5.8 (1.5) | |
| c. I know the risks & side effects of each option. | 25 | 6.0 (1.3) | |
| Decisional conflict scale, values clarification sub-scale | | | |
| a. I am clear about which benefits matter more to me. | 25 | 6.5 (0.8) | |
| b. I am clear about which risks and side effects matter most to me. | 25 | 6.6 (0.7) | |
| c. I am clear about which benefits, risks, and side effects matter most to me. | 25 | 6.6 (0.6) | |
| Decisional conflict scale, values clarification sub-scale | | | |
| a. I am clear about the best choice for me. | 25 | 6.3 (1.4) | |
| b. I feel sure about what to choose. | 25 | 6.1 (1.3) | |
| c. The decision is easy for me to make. | 25 | 5.9 (1.3) | |

* Possible responses to all items consisted of a 7-point scale ranging from 1 (strongly disagree) to 7 (strongly agree).
Abbreviations: SD = standard deviation; UTAT = Unified theory of acceptance and use of technology

INTEGRATED MULTI-CRITERIA DECISION SUPPORT FRAMEWORK

RELATED APPLICATION

This application claims the benefit of U.S. Provisional Application No. 61/591,257, entitled "INTEGRATED MULTI-CRITERIA DECISION SUPPORT FRAMEWORK," filed Jan. 26, 2012, the entirety of which is expressly incorporated herein by reference.

GOVERNMENT LICENSE RIGHTS

This invention was made with government support under Grant HL093488 awarded by National Institutes of Health. The Government has certain rights to this invention.

FIELD

The disclosure relates generally to facilitation of decision making, and, in particular, to making and facilitating the making of medical-treatment decisions.

BACKGROUND

A key challenge in many decision makings is helping decision makers develop meaningful understandings of the differences between alternative resources and management strategies in order to make informed judgments about selection of a proper resource or strategy.

SUMMARY

Interactive decision dashboards may facilitate decision making by reducing the cognitive effort needed to evaluate various options through extensive use of data visualization techniques. The Interactive decision dashboards can present information in a non-linear format that facilitates information search and retrieval tailored to meet individual needs. For example, a physician or patient decision aid formatted as an interactive decision dashboard can be an effective and efficient way to make sense of the information required to make good decisions.

The integrated multi-criteria decision frameworks disclosed herein can facilitate making good decisions when faced with a complex choice among several alternatives with different combinations of strengths and weaknesses. The decision frameworks can be used to support decisions made by both individuals and groups of people. The decision framework can allow rapid incorporation of new information into the decision making process.

Some decision support systems using multi-criteria methods rely primarily on a single method. The integrated multi-criteria decision frameworks disclosed herein can combine multiple, e.g., five, multi-criteria methods in a single adaptable decision support intervention. In some embodiments, the framework can include some or all of the following six modules for example: a decision strategy module; a balance sheet module; an interactive decision dashboard module; an ordinal ranking module; a direct weighting module; and an Analytic Hierarchy Process (AHP) module.

Some systems and methods display queries regarding the significance of criteria to a decision maker, receive responses to those queries, and store data that permit evaluation of an alternative that was not displayed or otherwise made available to the decision maker at the time that the queries were displayed, the responses received, or both. In some embodiments, systems and methods can permit evaluation of whether a new alternative (e.g., a treatment option), based on the stored data, (i) is or may be preferable to a decision maker, (ii) better suited to the needs of a decision maker or other individual (e.g., a patient), (iii) meriting further consideration by a decision maker, or (iv) a combination thereof. Such systems and methods may, in some embodiments, expedite identification of more desirable alternatives after they become available for example.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

1. A system for evaluating patient treatment options, comprising:
   memory,
   one or more processors coupled to the memory, the one or more processors configured to execute a plurality of modules including:
   an ordinal ranking module configured to display a set of relative-weighting queries regarding the relative importance of at least two criteria to the treatment goal, receive one or more relative-weighting indicator responses to the set of relative-weighting queries, and modify a set of criteria weights based on the relative-weighting indicator responses;
   a direct weighting module configured to display a set of direct-weighting queries regarding the individual importance of at least one criterion to the treatment goal, receive one or more direct-weighting indicator responses to the set of direct-weighting queries, and modify the set of criteria weights based on the direct-weighting indicator responses;
   an analysis module configured to display a set of analytic queries comparing the at least two criteria, receive one or more analytic indicator responses to the set of analytic queries, and modify the set of criteria weights based on the analytic indicator responses;
   wherein at least one of the modules is configured to retrieve data descriptive of a plurality of treatment options at least with respect to the at least two criteria;
   wherein at least one of the modules is configured to display a set of criterion-exclusion queries, and receive one or more criterion-exclusion indicator responses to the set of criterion-inclusion queries;
   wherein at least one of the modules is configured to calculate, based on at least a portion of the data and the weights, and display a composite score for each treatment option except as indicated by the criterion-exclusion indicator responses; and
   wherein at least one of the modules is configured to determine whether at least one response is inconsistent with another received response, and, in response to determining existence of an inconsistency, to perform at least one of: (a) displaying a notice regarding the inconsistency, (b) displaying a resolution query directed to resolution of the inconsistency, (c) identifying at least one objectively incorrect understanding of a user indicated by the inconsistency and displaying information directed to correction of the understanding, or (d) notifying a health care provider of the inconsistency.

2. The system of clause 1, further comprising a balance sheet module configured to display at least a portion of the data in a table according to criteria and treatment options.

3. The system of clause 1, further comprising a decision dashboard module configured to display a graphical representation of a least a portion of the data.

4. The system of clause 1, further comprising a decision strategy module configured to receive decision information including the criteria and the treatment options.

5. The system of clause 1, wherein the analysis module is further configured to provide information related to consistency of analytic indicator responses.

6. The system of clause 1, further comprising a sensitivity analysis module configured to examine the effects of variation of the weights.

7. The system of clause 1, wherein the criteria include effectiveness, risk of side effects, and cost of a treatment strategy.

8. The system of clause 1, wherein at least some of the analytic queries in the set compare only two of the criteria.

9. The system of clause 1, wherein the analysis module is further configured to display a set of preference queries comparing attributes, relative to one of the at least two criteria, of at least two treatment options, receive one or more preference indicator responses to the set of preference queries, and modify the set of criteria weights based on the preference indicator responses.

10. A method for evaluating patient treatment options, comprising:
   a) retrieving data indicative of the attributes of a plurality of treatment options relative to criteria;
   b) displaying a set of criterion-exclusion queries and receiving one or more criterion-exclusion indicator responses to the set of criterion-inclusion queries;
   c) displaying a set of relative-weighting queries regarding the relative importance of at least two criteria to the treatment goal, receiving one or more relative-weighting indicator responses to the set of relative-weighting queries, and modifying a set of criteria weights based on the relative-weighting indicator responses;
   d) displaying a set of direct-weighting queries regarding the individual importance of at least one criterion to the treatment goal, receiving one or more direct-weighting indicator responses to the set of direct-weighting queries, and modifying the set of criteria weights based on the direct-weighting indicator responses;
   e) displaying a set of analytic queries comparing the at least two criteria, receiving one or more analytic indicator responses to the set of analytic queries, and modifying the set of criteria weights based on the analytic indicator responses;
   f) repeating at least one of steps b, c, d, or e;
   g) determining whether at least one response is inconsistent with another received response, and, in response to determining existence of an inconsistency, performing at least one of: (i) displaying a notice regarding the inconsistency, (ii) displaying a resolution query directed to resolution of the inconsistency, (iii) identifying at least one objectively incorrect understanding of a user indicated by the inconsistency and displaying information directed to correction of the understanding, or (iv) notifying a health care provider of the inconsistency; and
   h) calculating, based on at least a portion of the data and the weights, and displaying a composite score for each treatment option except those indicated by the criterion-exclusion indicator responses.

11. The method of clause 10, further comprising alphanumerically displaying the data.

12. The method of clause 10, further comprising graphically displaying at least a portion of the data.

13. The method of clause 10, further comprising displaying a option-selection query and receiving a selection indicator response to the option-selection query.

14. A method for evaluating patient treatment options, comprising:
   a) displaying, by a first processor, information regarding (1) a plurality of treatment options and (2) one or more of (i) a set of criterion-exclusion queries, (ii) a set of relative-weighting queries regarding the relative importance of at least two criteria to the treatment goal, (iii) a set of direct-weighting queries regarding the individual importance of at least one criterion to the treatment goal, or (iv) a set of analytic queries comparing at least two criteria;
   b) receiving one or more indicator responses to the displayed queries;
   c) storing, in a non-transitory machine-readable medium, at least one of (i) the received indicator responses or (ii) a set of criteria weights determined based on the indicator responses;
   d) calculating a composite score for an additional treatment option, not comprised by the plurality of treatment options, based on (1) data indicative of attributes of the additional treatment option relative to the at least two criteria, and (2) at least a portion of the stored one of (i) the received indicator responses or (ii) the set of criteria weights; and
   e) outputting an indicator of the composite score.

15. The method of Clause 14, wherein the indicator of the composite score comprises an indication of potential preference for the additional treatment option over at least one other treatment option.

16. The method of Clause 14, wherein the indicator of the composite score comprises an indication of potential preference for the additional treatment option over each of a plurality of treatment options.

17. The method of Clause 14, wherein the indicator of the composite score comprises an indication that the composite score of the additional treatment option is better than the composite score of at least one other treatment option.

18. The method of Clause 14, wherein the indicator of the composite score comprises an indication that the composite score of the additional treatment option is better than composite scores of each of a plurality of treatment options.

19. The method of Clause 14, wherein outputting the indicator of the composite score comprises displaying the composite score.

20. The method of Clause 14, wherein the displaying of step (e) is performed by the first processor.

21. The method of Clause 14, wherein the displaying of step (e) is performed by a second processor.

22. The method of Clause 14, further comprising calculating a composite score for each of the plurality of treatment options based on (1) data indicative of attributes of the plurality of treatment options relative to the at least two criteria, and (2) at least a portion of one of (i) the received indicator responses or (ii) the set of criteria weights; and displaying the composite scores for the plurality of treatment options.

23. The method of Clause 22, wherein the composite scores for the plurality of treatment options are displayed with the composite score for the additional treatment option.

24. The method of Clause 22, wherein the composite scores for the plurality of treatment options are calculated based on the stored one of (i) the received indicator responses or (ii) the set of criteria weights.

25. The method of Clause 14, wherein the additional treatment option was not displayed to a user prior to storing the at least one of (i) the received indicator responses or (ii) the set of criteria weights, wherein the indicator responses were received from the user.

26. A system for evaluating patient treatment options, comprising:
   memory,
   one or more processors coupled to the memory, the one or more processors configured to execute (1) a display module configured to display information regarding a plurality of treatment options and (2) one or more of:
      a) an ordinal ranking module configured to display a set of relative-weighting queries regarding the relative importance of at least two criteria to the treatment goal, receive one or more relative-weighting indicator responses to the set of relative-weighting queries;
      b) a direct weighting module configured to display a set of direct-weighting queries regarding the individual importance of at least one criterion to the treatment goal, receive one or more direct-weighting indicator responses to the set of direct-weighting queries; and
      c) an analysis module configured to display a set of analytic queries comparing the at least two criteria, receive one or more analytic indicator responses to the set of analytic queries;
   wherein at least one of the modules is configured to display a set of criterion-exclusion queries, and receive one or more criterion-exclusion indicator responses to the set of criterion-inclusion queries;
   wherein at least one of the modules is configured to store, in memory, at least one of received responses and a set of criteria weights determined based on the received indicator responses;
   wherein the system further comprises:
      d) a calculation module configured to calculate a composite score for an additional treatment option, not comprised by the plurality of treatment options, based on (1) data indicative of attributes of the additional treatment option relative to the at least two criteria, and (2) at least a portion of the stored one of (i) the received indicator responses or (ii) the set of criteria weights; and
      e) an output module configured to output an indicator of the composite score.

27. The system of Clause 26, wherein the indicator of the composite score comprises an indication of potential preference for the additional treatment option over at least one other treatment option.

28. The system of Clause 26, wherein the indicator of the composite score comprises an indication of potential preference for the additional treatment option over each of a plurality of treatment options.

29. The system of Clause 26, wherein the indicator of the composite score comprises an indication that the composite score of the additional treatment option is better than the composite score of at least one other treatment option.

30. The system of Clause 26, wherein the indicator of the composite score comprises an indication that the composite score of the additional treatment option is better than composite scores of each of a plurality of treatment options.

31. The system of Clause 26, wherein the output module is configured to display the composite score.

32. The system of Clause 26, wherein the calculation module is further configured to calculate a composite score for each of the plurality of treatment options based on (1) data indicative of attributes of the plurality of treatment options relative to the at least two criteria, and (2) at least a portion of one of (i) the received indicator responses or (ii) the set of criteria weights; and displaying the composite scores for the plurality of treatment options.

33. The system of Clause 32, wherein the output module is configured to display the composite scores for the plurality of treatment options with the composite score for the additional treatment option.

34. The system of Clause 32, wherein the calculation module is further configured to calculate the composite scores for the plurality of treatment options based on the stored one of (i) the received indicator responses or (ii) the set of criteria weights.

35. A non-transitory machine-readable medium encoded with instructions executable by a processing system to perform a method for evaluating patient treatment options, comprising:
   a) retrieving data indicative of the performance of a plurality of treatment options relative to criteria descriptive of the treatment options;
   b) displaying a set of criterion-exclusion queries and receiving one or more criterion-exclusion indicator responses to the set of criterion-inclusion queries;
   c) displaying a set of relative-weighting queries regarding the relative importance of at least two criteria to the treatment goal, receiving one or more relative-weighting indicator responses to the set of relative-weighting queries, and modifying a set of criteria weights based on the relative-weighting indicator responses;
   d) displaying a set of direct-weighting queries regarding the individual importance of at least one criterion to the treatment goal, receiving one or more direct-weighting indicator responses to the set of direct-weighting queries, and modifying the set of criteria weights based on the direct-weighting indicator responses;
   e) displaying a set of analytic queries comparing the at least two criteria, receiving one or more analytic indicator responses to the set of analytic queries, and modifying the set of criteria weights based on the analytic indicator responses;
   f) repeating at least one of steps b, c, d, or e; and
   g) calculating, based on at least a portion of the data and the weights, and displaying a composite score for each treatment option except those indicated by the criterion-exclusion indicator responses.

36. The machine-readable medium of clause 35, wherein the instructions further comprise code for alphanumerically displaying the data.

37. The machine-readable medium of clause 35, wherein the instructions further comprise code for graphically displaying at least a portion of the data.

38. The machine-readable medium of clause 35, wherein the instructions further comprise code for displaying a option-selection query and receiving a selection indicator response to the option-selection query.

39. A computing machine comprising the machine-readable medium of clause 35.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 3 is a simplified example of table generated by a balance sheet module, such as shown in FIG. 2, according to some embodiments.

FIG. 5 is an example of a user interface generated by a ranking module, such as shown in FIG. 2, in accordance with various embodiments of the subject technology.

FIG. 7 is a table of information related to several medications.

FIG. 8 is a table summarizing characteristics of a study sample.

FIGS. 9A-B are a table of results of a quantitative dashboard evaluation.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1A:
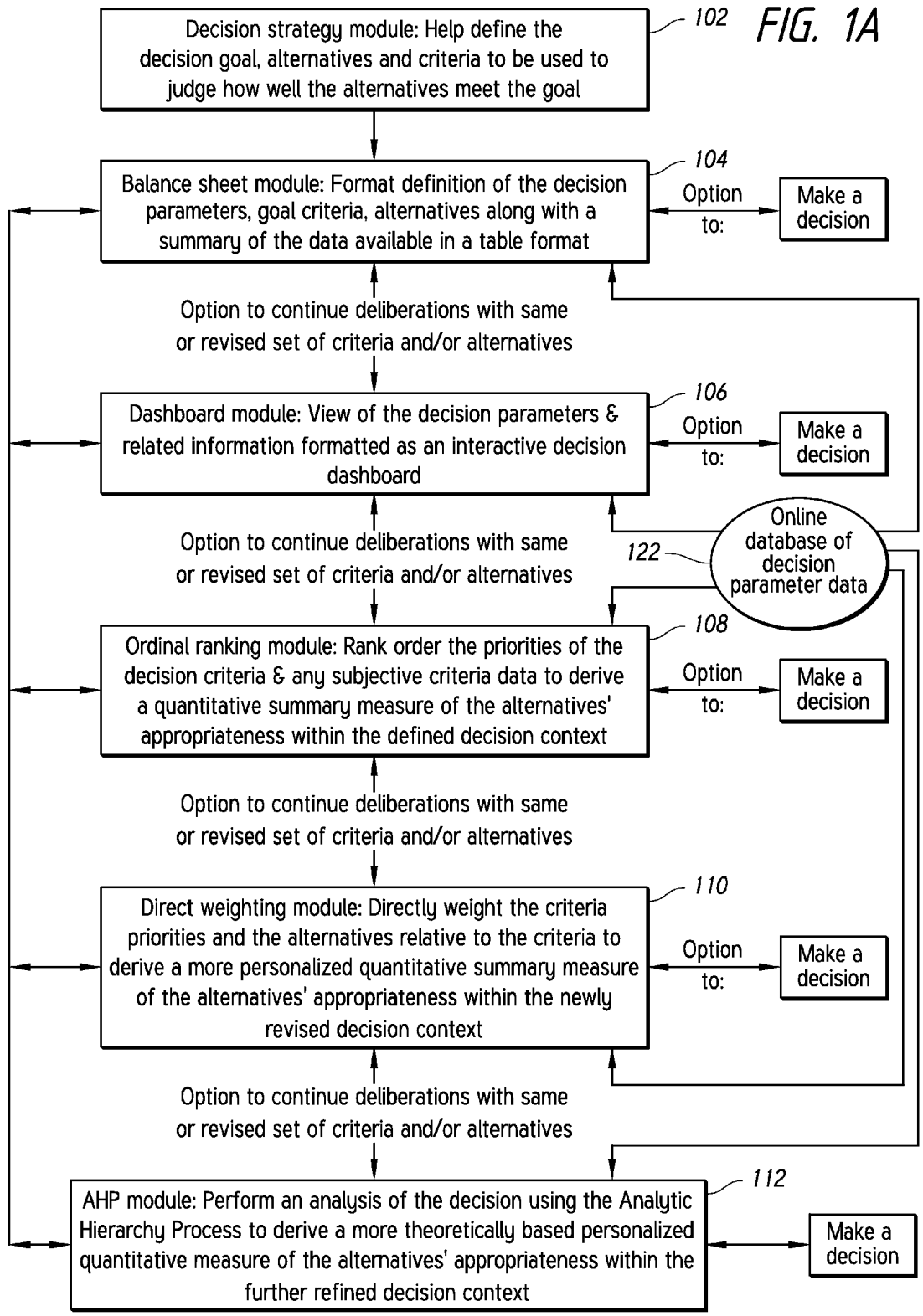
FIG. 1A is a diagram illustrating interaction between modules of a decision support framework, according to some embodiments.

FIG. 1A is a diagram illustrating interaction between modules of a decision support framework 100, according to some embodiments. As illustrated in FIG. 1, the framework can comprise a decision strategy module 102, a balance sheet module 104, a dashboard module 106, an ordinal ranking module 108, a direct weighting module 110, and an APH module 112. In some embodiments, the integrated multi-criteria decision support framework can use an explicit, step-wise method for decision making Although the method can be step-wise, the framework can permit selective, arbitrary movement among modules in some embodiment. For example, the framework can respond to received responses to move or return to a selected step (or module).

Figure 1B:
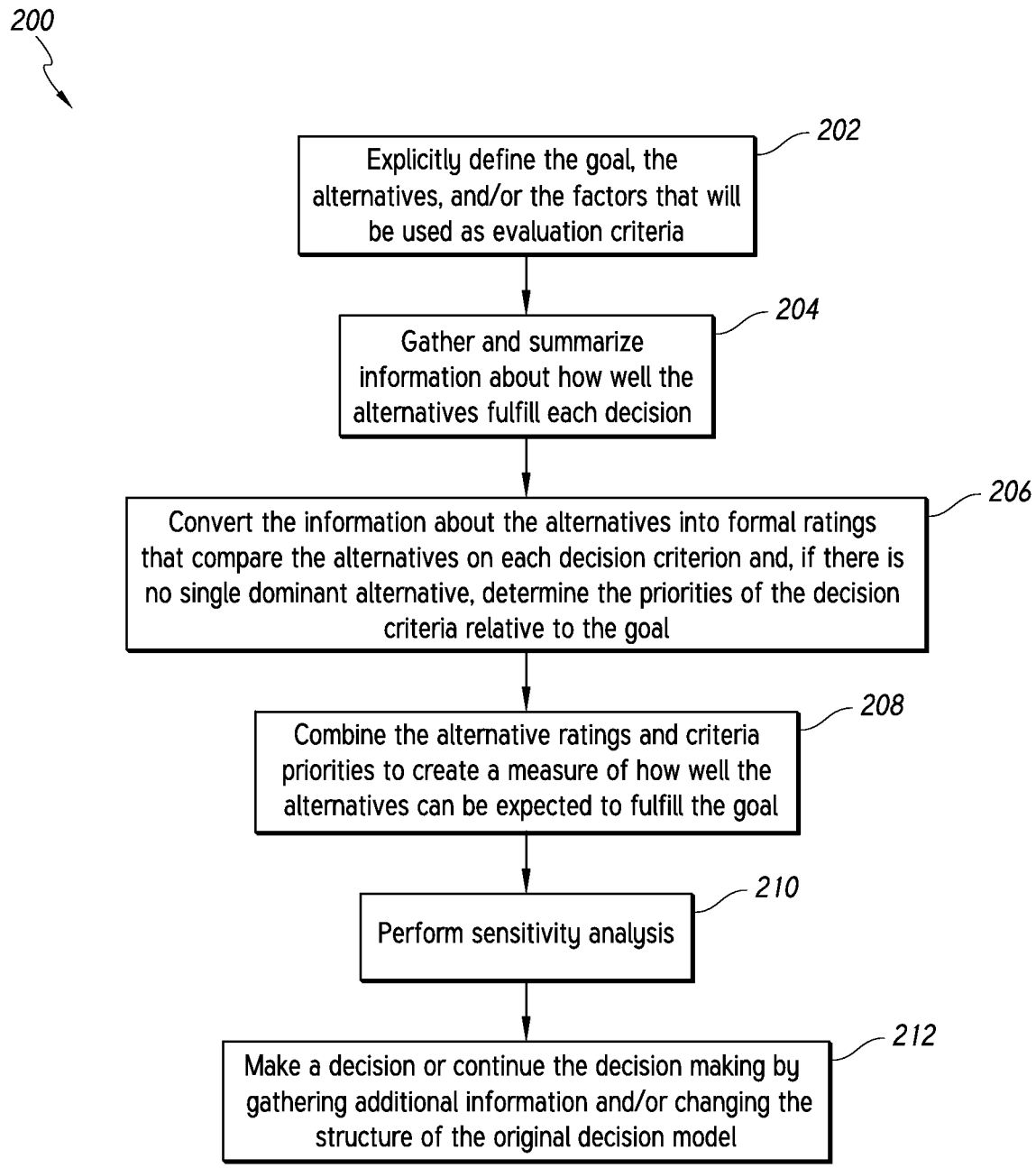
FIG. 1B illustrates an exemplifying step-wise method for decision making according to some embodiments.

FIG. 1B illustrates an exemplifying step-wise approach 200. A step 202 can include explicitly defining the goal, the alternatives, and/or the factors that will be used as criteria to evaluate how well the alternatives meet the goal. A step 204 can include gathering and summarizing information about how well the alternatives fulfill each decision criterion. A step 206 can include converting the information about the alternatives into formal ratings that compare the alternatives on each decision criterion and, if there is no single dominant alternative, determining the priorities of the decision criteria relative to the goal. In a step 208, the alternative ratings and criteria priorities can be combined to create a measure of how well the alternatives can be expected to fulfill the goal. A step 210 can include a sensitivity analysis. Step 210 can include varying the parameters used for the initial analysis to explore the impact on the results of changes in the original judgments and assumptions. Step 212 can include either making a decision or continuing the decision making by gathering additional information and/or changing the structure of the original decision model. If the latter option is chosen, one or more of the steps are repeated until a final decision is made. Any combination of some or all of the foregoing steps is contemplated.

Figure 2:
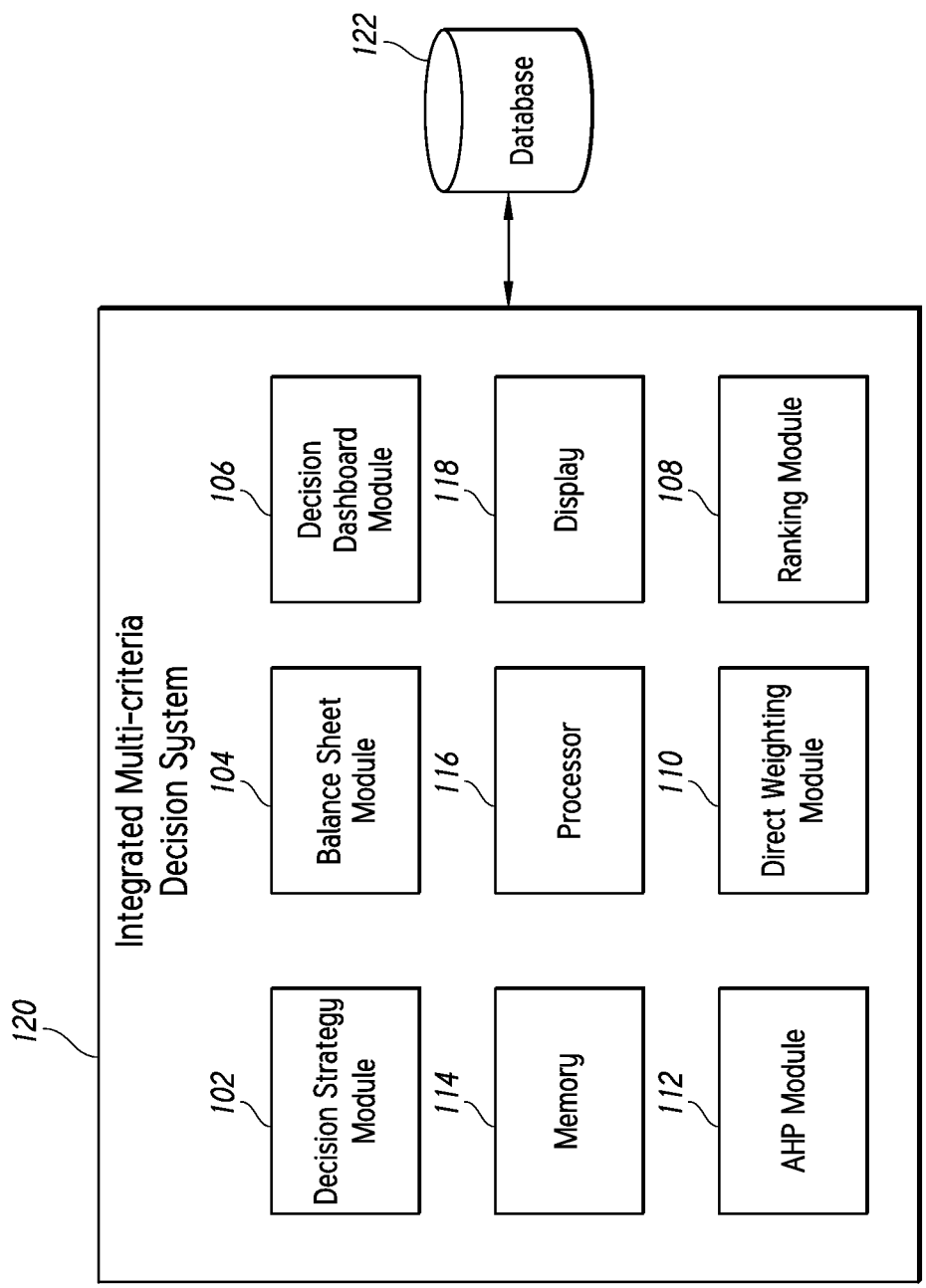
FIG. 2 is a schematic diagram illustrating an integrated multi-criteria decision system, according to some embodiments.

FIG. 2 is a schematic diagram illustrating an integrated multi-criteria decision system 120, according to some embodiments. The integrated multi-criteria decision system can include the decision strategy module 102, the balance sheet module 104, the decision dashboard module 106, the ranking module 108, the direct weighting module 110, the APH module 112, memory 114, one or more processors 116, and a display 118.

The decision strategy module 102 is optional and can be configured to help the decision makers define the decision goal, the alternatives to be considered, and/or the criteria that will be used to compare the alternatives relative to the goal.

Once the decision parameters are defined (either through use of the decision strategy module or some other means), in the next step decision parameters can be summarized along with the information available. This can be accomplished in the balance sheet module 104. The result can be a balance sheet table with one column for every decision criterion and one row for every alternative, as illustrated in FIG. 3 for example. A database 122 can provide summaries of current data regarding outcomes expected for different alternatives categorized based on common decision criteria. In the context of evaluating medical treatment options, decision criteria can include, for example, effectiveness, risk of side effects, and cost. These links can be maintained throughout the entire framework. In some aspects the database can be an online database accessible via a network, such the Internet, a local area network (LAN), a wide area network (WAN), a metropolitan area network (MAN), or the like, or a combination thereof.

As illustrated in FIG. 1A, after reviewing the balance sheet table, a decision maker can decide to make a decision, redefine the decision parameters, or continue to explore the decision by moving on to any other module in the multi-criteria decision system. The decision dashboard module 106 can present the decision-related information contained in the balance sheet table graphically, using the display module, and can allow the decision makers to interactively explore the data. After reviewing the dashboard, the decision makers can decide to make a decision, refine the decision parameters by adding or deleting alternatives and/or criteria, retrace previous steps, or continue to explore the decision by moving on to the next step in the framework, the ranking module (e.g., ordinal ranking module), or any other module in the framework.

The ordinal ranking module 108 can engage the user in analyzing the decision by rank ordering the priorities of the criteria relative to the goal of the decision and the alternatives relative to the criteria. The latter step can be taken if the ranks of the alternatives relative to a criterion cannot be determined objectively. These ordinal rankings can then be combined to create a numeric score indicating how well the alternatives can be expected to meet the goal based on the input provided by the user. If desired, sensitivity analyses can be performed to determine the effects of changing the initial set of rankings. At this point, the decision makers can decide to make a decision, refine the decision parameters by adding or deleting alternatives and/or criteria, retrace previous steps, or continue to explore the decision by moving on to the either the next step in the framework, direct weighting module, or any other module in the system.

In the direct weighting module 110, users can directly assess the priorities assigned to decision criteria and the evaluations of the alternatives relative to the criteria. Because the decision maker(s) can assign all weights used in the analysis, this step may involve judgments regarding both the criteria and the alternatives. Once the weights are determined they can be combined to generate the overall score indicating the alternatives' priorities relative to the goal based on the input provided by the user. If desired, sensitivity analyses can then be performed to examine the effects of changing the initial set of weights. At this point, the decision makers can decide to make a decision, refine the decision parameters by adding or deleting alternatives and/or criteria, retrace previous steps, or continue to explore the decision by moving on to the AHP module.

The AHP module 112 can engage the user in a full multi-criteria analysis of the decision using the AHP, a well-known and widely used multi-criteria method. The AHP can extend the sophistication of the analysis beyond simple direct weighting by: a) deriving weights through a series of pairwise comparisons among the elements being compared, b) providing information about the consistency of the pairwise judgments in the analysis, and c) providing a thorough theoretical background for the weighting and score-generating process. Once the weights are determined, they can be combined to generate the overall score indicating the alternatives' priorities relative to the goal based on the input provided by the user. If desired, sensitivity analyses can then be performed. Further details of this process are provided below. At this point, the decision makers can decide to make a decision, retrace previous steps, or continue to explore the decision in some other way.

One or more of the decision strategy module 102, the balance sheet module 104, the dashboard module 106, the ordinal ranking module 108, the direct weighting module 110, the APH module 112, or another module (not shown) can be configured to determine whether at least one response is inconsistent with another received response, such as a response received by another module. For example, the direct weighting module 110 can be configured to evaluate whether responses to directed weighting queries are inconsistent with responses received by the ordinal ranking module 108 to a set of ordinal ranking queries to determine whether the response are congruent. As another example, the APH module 112 can be configured to compare the responses receive by the ordinal ranking module 108, the direct weighting module 110, or both are congruent with each other and/or with responses to pairwise comparisons. In response to determining existence of an inconsistency among analyzed responses, the module(s) can perform at least one of: (a) displaying a notice regarding the inconsistency, (b) displaying a resolution query directed to resolution of the inconsistency, (c) identifying at least one objectively incorrect understanding of a user indicated by the inconsistency and displaying information directed to correction of the understanding, or (d) notifying a health care provider of the inconsistency.

A notification of the inconsistency can be provided to a decision maker, person supporting the decision maker, or other interested individual. For example, the notification can be provided a patient, a family member of a patient, a physician, or other health care worker. The notification can prompt the notified individual to take remedial action.

Upon detection of an incongruence, one or more queries can be presented such that responses to those quires resolves the incongruence. Inconsistency-resolution queries can be presented before, after, or together with a notification of the incongruence. For example, a individual, e.g., system user, can be notified that Response A conflicts with Response B and requested to revise one of the Response A and Response B. As another example, an individual can be presented with a query that has not been presented to the individual in the same session and that resolves a conflict between prior responses.

In some embodiments, one or more of the decision strategy module 102, the balance sheet module 104, the dashboard module 106, the ordinal ranking module 108, the direct weighting module 110, the APH module 112, or another module (not shown) can be configured to store, in a non-transitory computer-readable medium, data indicative of at least one of (i) responses received by that module, other modules, or both, and (ii) a set of criteria weights determined based on the received responses. The data can be transmitted over a network to be stored in non-transitory computer-readable medium at a remote location.

A calculation module can be configured to calculate a composite score for an additional alternative, e.g., treatment option, not presented to a user during a session when the responses were received, based on (1) data indicative of attributes of the additional alternative, and (2) at least a portion of the stored data. An output module can be configured to output an indicator of the composite score. The calculation module, the output module, or both can operate remotely, in time, space or both, from the decision strategy module 102, the balance sheet module 104, the dashboard module 106, the ordinal ranking module 108, the direct weighting module 110, and/the APH module 112.

In some embodiments, the indicator of the composite score can be used to determine whether to present the decision maker with information regarding the additional alternative. In some embodiments, the indicator of the composite score can comprise an indication of a potential preference for the additional alternative (e.g., treatment option) over at least one other alternative (e.g., treatment option). In some embodiments, the indicator of the composite score can comprise an indication of potential preference for the additional alternative over all of the alternative that were presented or available to the decision maker during the session when the responses were received and stored. In some embodiments, the indicator of the composite score can comprise an indication that the composite score of the additional alternative is better than the composite score of at least one other alternative. In some embodiments, the indicator of the composite score can comprise an indication that the composite score of the additional alternative is better than composite scores of all of the alternative that were presented or available to the decision maker during the session when the responses were received and stored. In some embodiments, the output module can be configured to display the composite score.

The calculation module can be configured in some embodiments to calculate a composite score for the alternatives presented or available to the user at the time responses were received based on (1) data indicative of attributes of the plurality of alternatives relative to the at least two criteria, and (2) at least a portion of one of (i) the received indicator responses or (ii) the set of criteria weights. The data indicative of the alternatives' attributes can be the same what was used as the basis of the user's responses to the decision strategy module 102, the balance sheet module 104, the dashboard module 106, the ordinal ranking module 108, the direct weighting module 110, and/the APH module 112. In some embodiments, the data can be different that what was used at that time. For example, at the time of calculating composite scores after a session when responses were received, the merits of a particular alternative may have changed. For example, the cost of a particular alternative may increase or decrease over time.

The integrated multi-criteria decision system can be implemented on a client device or a server. By way of illustration and not limitation, a client device can represent a computer, a mobile phone, a laptop computer, a thin client device, a personal digital assistant (PDA), a portable computing device, or a suitable device with a processor. In one example, a client device can be a Smartphone (e.g., iPhone, Android phone, Blackberry, etc.). In one example, a client device can be mobile. In another example, a client device can be stationary. According to one aspect of the disclosure, a client device can be a device having at least a processor and memory, where the total amount of memory of the client device could be less than the total amount of memory in a server. In one example, a client device does not have a hard disk. In one aspect, a client device has a display smaller than a display supported by a server. In one aspect, a client device can include one or more client devices.

In some embodiments, a server can represent a computer, a laptop computer, a computing device, a virtual machine (e.g., VMware® Virtual Machine), a desktop session (e.g., Microsoft Terminal Server), a published application (e.g., Microsoft Terminal Server) or a suitable device with a processor. In some embodiments, a server can be stationary. In some embodiments, a server can be mobile. In certain configurations, a server can be any device that can represent a client device. In some embodiments, a server can include one or more servers.

FIG. 3 is a simplified example of a table 300 generated by a balance sheet module 104, such as shown in FIG. 2, according to some embodiments. The balance sheet table can be automatically generated by the balance sheet module. The balance sheet table includes a number of columns each representing a criteria (e.g., criteria A, B, C and D) defined by a user (e.g., a decision maker). Also defined by the user are a number of alternatives (e.g., alternatives 1, 2, and 3). The cells in the table can contain information that describes the performance of each alternative relative to a criterion. For example, the cell denoted A1 can contain information about how well alternative 1 performs on Criterion A.

Figure 4:
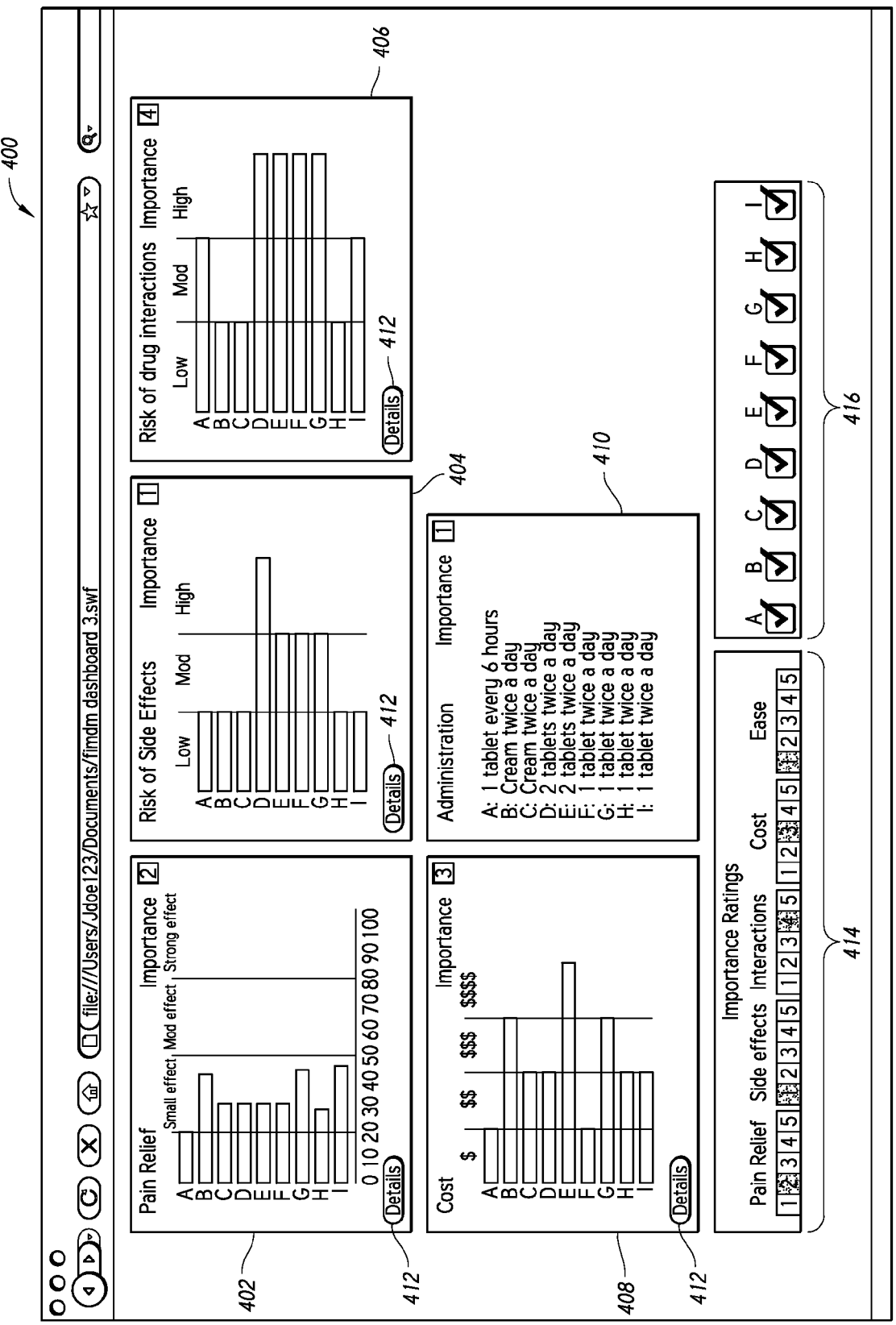
FIG. 4 is an example of an interactive decision dashboard, in accordance with various embodiments of the subject technology.

FIG. 4 is an example of an interactive decision dashboard 400, according to some embodiments. The decision dashboard module 106 can support decision making by presenting the information that is used in making the choice in a structured format (steps 202 and 204 of the multi-criteria decision making framework of FIG. 1B). Decision dashboards can differ from balance sheets in the way the information is presented. As illustrated in FIG. 4, the dashboard 400 can present information graphically using formats designed to enhance understanding of the differences that exist among the decision options. Interactive dashboards provide users with the ability to actively explore the information being presented by obtaining additional information about the alternatives and modifying the information displayed. Although FIG. 4 illustrates an implementation of a dashboard 400 via a browser, the dashboard can be implemented in other ways in some embodiments. For example, the dashboard, and/or other aspects of the subject technology (e.g., of the framework 100 or system 120 for example) can be implemented using a dedicated application running on specific or general use hardware. In some embodiments, the subject technology can be implemented via a mobile device such as a phone or tablet computer, for example.

In some embodiments, the dashboard 400 can illustrate differences between treatment options for treating a disease such as a pain related to osteoarthritis of the knee. Information about the relative abilities of the alternatives relative to each decision criterion can be shown in separate panels. In the example dashboard shown in FIG. 4, five panels 402, 404, 406, 408, 410 are shown that summarize the relative performance of the treatment alternatives with regard to each of the included drug (medication) information categories. In four of the panels 402, 404, 406, 408, relative performances are shown graphically. As illustrated in FIG. 4, graphical representations can comprise bar graphs with a bar indicating how well a particular alternative performs relative to the criterion of a particular panel. Other graphical representations can be used in some embodiments.

Buttons 412 for obtaining additional category-specific information can be included within some or all of the panels, as illustrated in FIG. 4 for each of four panels 402, 404, 406, 408, but not for the panel 410 that corresponds to the administration category. In response to inputs received in response to selection of a button 412, the dashboard module 106 can display more information about the alternatives relative to the criterion of the panel corresponding to the selected button 412.

Buttons 414, shown in FIG. 4 at the bottom left of the display, can be used to prioritize the importance of each drug information category in making a treatment choice. A set of buttons 414 with each button representing a different priority can be provided for each criterion. As illustrated in FIG. 4 for example, a selected priority level for a criterion can be displayed in a corresponding panel 402, 404, 406, 408.

Buttons 416, shown in FIG. 4 at the bottom right of the display, can be used to determine which alternatives (e.g., drugs in FIG. 4) are included in the display. Some panels, such as panel 410, can indicates text descriptions, for example regarding various administration options. Buttons 416 can be displayed as check boxes. In response to inputs received in response to selection of a button 416, the dashboard module 106 can hide or display information about the corresponding alternative. One or more buttons 416 can be provided for each criterion. For example, one button 416 can toggle display of an alternative or separate buttons 416 can be provide to select display or omission of a criterion.

FIG. 5 is an example of a user interface 500 generated by the ranking module 108, such as shown in FIG. 2, according to some embodiments. The user interface can receive user inputs via a number of selection options 502. For example, the queries can request that a user input via radio buttons the criterion that the user considers most important, second most important, etc. The ranking module 108 presents queries requesting users to rank order the criteria in terms of their importance in meeting the decision goal and the alternatives relative to their abilities to fulfill each of the decision criteria. These rank order judgments can then be converted into numeric scores 504 that, when combined, can create a measure of how well the alternatives can be expected to meet the goal based on the input provided by the user. Although the embodiment illustrated in FIG. 6 indicates that the "first step in exploring your options is to rank order the difference among the treatment options based on how important they are to you in making your decision," such a step is not the first in some embodiments that include it, and such a step can be omitted in some embodiments.

Figure 6:
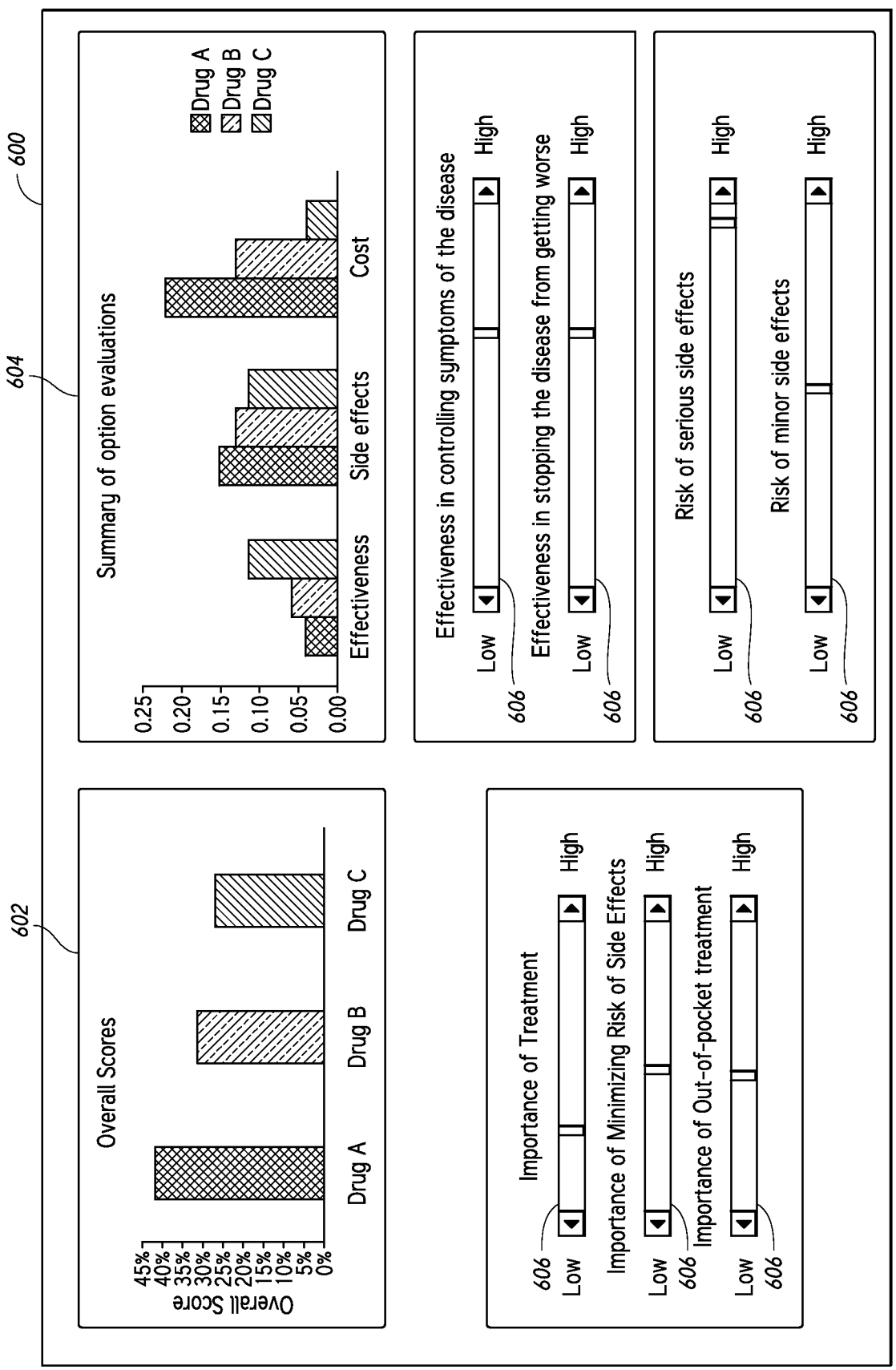
FIG. 6 is an example of a user interface generated by a direct weighing module, such as shown in FIG. 2, in accordance with various embodiments of the subject technology.

FIG. 6 is an example of a user interface 600 generated by the direct weighting module 110, such as shown in FIG. 2, according to some embodiments. The direct weighting module of FIG. 2 can ask user(s) (e.g., decision maker(s)) to directly assess the priorities assigned to decision criteria and the evaluations of the alternatives relative to the criteria. Because the decision maker(s) can assign all weights used in the analysis, this step may involve rank order judgments regarding both the criteria and the alternatives. The user interface can show graphs representing an overall score 602, a summary of option evaluations 604, and sliders 606 to receive user inputs. The graphs 602, 604 summarize the results of the analysis. User input can be received via a series of sliders 606 used to adjust the weights. The sliders can adjust the weights of the major decision criteria and sub-criteria included in a decision making scenario. For example, in a disease treatment scenario, the user input can include, importance related to treatment, importance of minimizing risk of side effects, importance of out-of-pocket treatment and so on. The user input can also include inputs regarding effectiveness is controlling symptoms of the disease or risks of serious side effects.

FIG. 7 shows a table 700 of information related to several drugs, such as generated by a balance sheet module 104 in some embodiments. The drugs shown in FIG. 7 can correspond to the options shown in the decision dashboard of FIG. 4, in some embodiments. Table 700 can summarize the treatment-related information included in the dashboard of FIG. 4.

To avoid respondent bias due to past treatment experiences or name recognition, the options on the dashboard can be identified using arbitrary letters rather than, for example, the actual drug names, where the decision making is related to selection of a drug for treating a disease. Note that the data indicate that two options, e.g., non-steroidal anti-inflammatory (NSAID) drugs plus misoprostol and non-steroidal anti-inflammatory drugs and proton pump inhibitors (PPIs), can be considered inferior choices because other treatment options are available that are better with respect to every medication characteristic being considered.

A study was conducted to quantitatively evaluate a dashboard according to an embodiment. FIG. 8 shows a table 800 summarizing characteristics of participants in the study. The majority of participants were white women with at least an Associate's degree and good to excellent literacy and numeracy skills. They were recruited in almost equal proportions from office and departmental staff, patient volunteers, and clinical trial website respondents.

FIGS. 9A-B is a table illustrating results of a quantitative dashboard evolution. The responses incorporated in FIGS. 9A and 9B show consistently positive answers for questions concerning mechanical and cognitive ease of use, decision aiding effectiveness, and effectiveness in reducing decisional conflict by providing needed information, clarifying values, and easing uncertainty. There seems to be no evidence of adverse emotional consequences.

Figure 10:
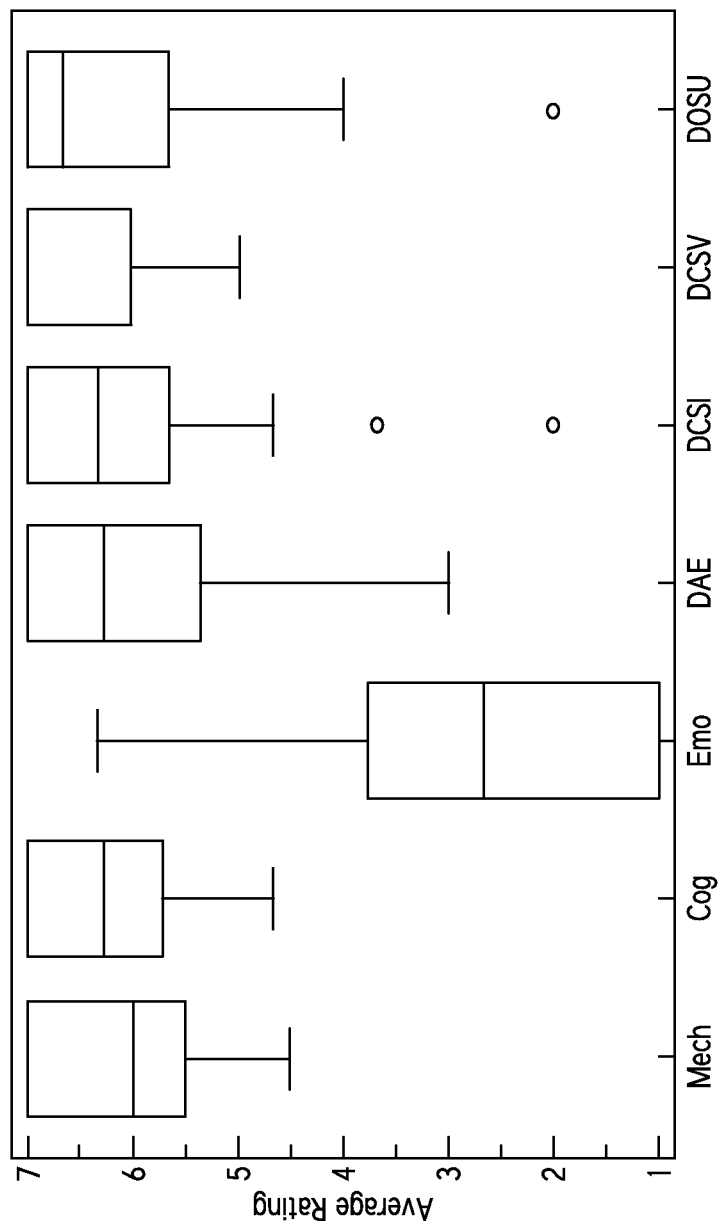
FIG. 10 is a diagram illustrating ratings shown in tables 9A-B.

FIG. 10 is a diagram illustrating ratings shown in the tables of FIGS. 9A-B, according to some embodiments. The diagram summarizes the ratings and evaluation results shown in FIGS. 9A-B. The vertical axis indicates the average rating and the horizontal axis shows abbreviations representing categories presented in FIGS. 9A and 9B. The abbreviations include: Mech=mechanical ease of use scale (4 items); Cog=cognitive ease of use scale (7 items); Emo=emotional ease of use scale (3 items); DAE=decision aiding effectiveness scale (7 items); DCSI=decisional conflict scale, informed sub-scale; DCSV=decisional conflict scale, values sub-scale; DCSU=decisional conflict scale, uncertainty sub-scale.

Some embodiments can be implemented in a system including a server and a client device. When a client device and a server are remote with respect to each other, a client device may connect to a server over a network, for example, via a modem connection, a LAN connection including the Ethernet or a broadband WAN connection including DSL, Cable, T1, T3, Fiber Optics, Wi-Fi, or a mobile network connection including GSM, GPRS, 3G, WiMax or other network connection. A network can be a LAN network, a WAN network, a wireless network, the Internet, an intranet or other network. A network may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name or other system name. These illustrate some examples as to how one device may be remote to another device. But the subject technology is not limited to these examples.

Figure 11:
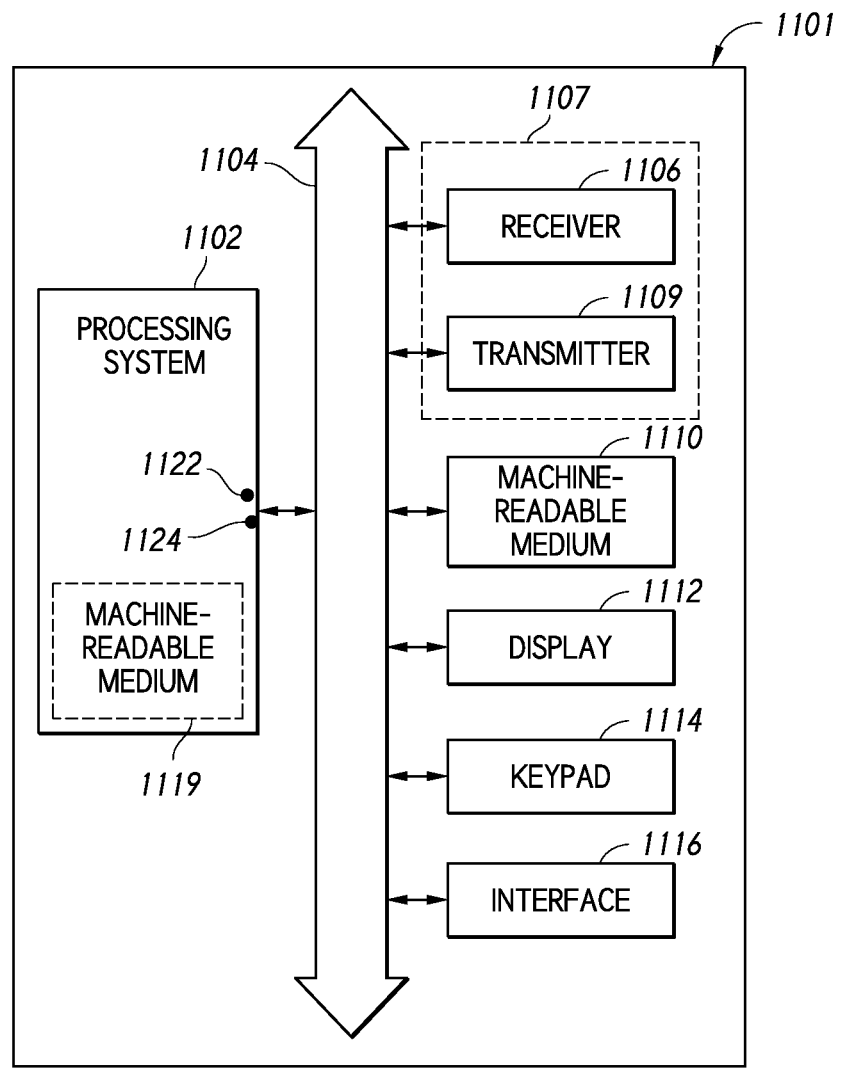
FIG. 11 is a conceptual block diagram illustrating an example of a system, in accordance with various embodiments of the subject technology.

FIG. 11 is a conceptual block diagram illustrating an example of a system, in accordance with various embodiments of the subject technology. A system 1101 may be, for example, a client device (e.g., client device 102) or a server (e.g., server 106). The system 1101 may include a processing system 1102. The processing system 1102 is capable of communication with a receiver 1106 and a transmitter 1109 through a bus 1104 or other structures or devices. It should be understood that communication means other than busses can be utilized with the disclosed configurations. The processing system 1102 can generate audio, video, multimedia, and/or other types of data to be provided to the transmitter 1109 for communication. In addition, audio, video, multimedia, and/or other types of data can be received at the receiver 1106, and processed by the processing system 1102.

The processing system 1102 may include a processor for executing instructions and may further include a machine-readable medium 1119, such as a volatile or non-volatile memory, for storing data and/or instructions for software programs. The instructions, which may be stored in a machine-readable medium 1110 and/or 1119, may be executed by the processing system 1102 to control and manage access to the various networks, as well as provide other communication and processing functions. The instructions may also include instructions executed by the processing system 1102 for various user interface devices, such as a display 1112 and a keypad 1114. The processing system 1102 may include an input port 1122 and an output port 1124. Each of the input port 1122 and the output port 1124 may include one or more ports. The input port 1122 and the output port 1124 may be the same port (e.g., a bi-directional port) or may be different ports.

The processing system 1102 may be implemented using software, hardware, or a combination of both. By way of example, the processing system 1102 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 1119) may include storage integrated into a processing system, such as might be the case with an ASIC. Machine-readable media (e.g., 1110) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 1102. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium. In one aspect, a computer-readable medium is a non-transitory computer-readable medium, a computer-readable storage medium, or a non-transitory computer-readable storage medium. Instructions may be executable, for example, by a client device or server or by a processing system of a client device or server. Instructions can be, for example, a computer program including code.

An interface 1116 may be any type of interface and may reside between any of the components shown in FIG. 11. An interface 1116 may also be, for example, an interface to the outside world (e.g., an Internet network interface). A transceiver block 1107 may represent one or more transceivers, and each transceiver may include a receiver 1106 and a transmitter 1109. A functionality implemented in a processing system 1102 may be implemented in a portion of a receiver 1106, a portion of a transmitter 1109, a portion of a machine-readable medium 1110, a portion of a display 1112, a portion of a keypad 1114, or a portion of an interface 1116, and vice versa.

Figure 12:
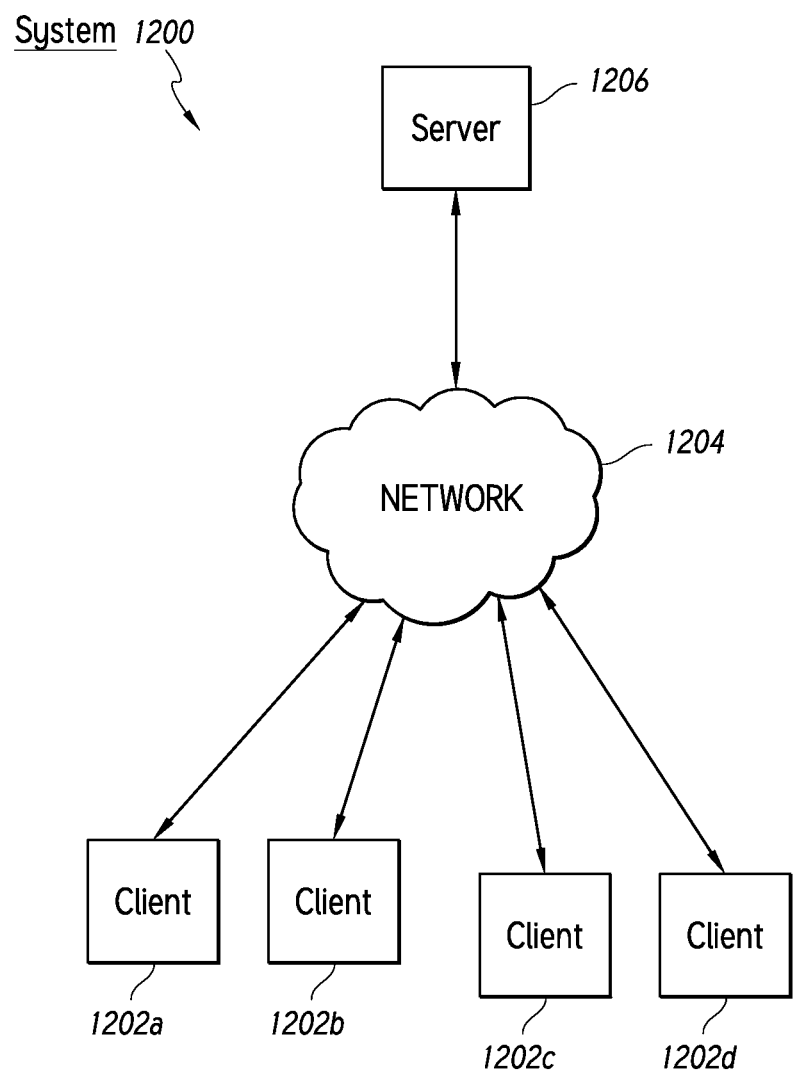
FIG. 12 illustrates a simplified diagram of a system, in accordance with various embodiments of the subject technology.

FIG. 12 illustrates a simplified diagram of a system 1200, in accordance with various embodiments of the subject technology. The system 1200 may include one ore more remote client devices 1202 (e.g., client devices 1202a, 1202b, 1202c, and 1202d) in communication with a server computing device 1206 (server) via a network 1204. In some embodiments, the server 1206 is configured to run applications that may be accessed and controlled at the client devices 1202. For example, a user at a client device 1202 may use a web browser to access and control an application running on the server 1206 over the network 1204. In some embodiments, the server 1206 is configured to allow remote sessions (e.g., remote desktop sessions) wherein users can access applications and files on the server 1206 by logging onto the server 1206 from a client device 1202. Such a connection may be established using any of several well-known techniques such as the Remote Desktop Protocol (RDP) on a Windows-based server.

By way of illustration and not limitation, in one aspect of the disclosure, stated from a perspective of a server side (treating a server as a local device and treating a client device as a remote device), a server application is executed (or runs) at a server 1206. While a remote client device 1202 may receive and display a view of the server application on a display local to the remote client device 1202, the remote client device 1202 does not execute (or run) the server application at the remote client device 1202. Stated in another way from a perspective of the client side (treating a server as remote device and treating a client device as a local device), a remote application is executed (or runs) at a remote server 1206.

By way of illustration and not limitation, a client device 1202 can represent a computer, a mobile phone, a laptop computer, a thin client device, a personal digital assistant (PDA), a portable computing device, or a suitable device with a processor. In one example, a client device 1202 is a smartphone (e.g., iPhone, Android phone, Blackberry, etc.). In certain configurations, a client device 1202 can represent an audio player, a game console, a camera, a camcorder, an audio device, a video device, a multimedia device, or a device capable of supporting a connection to a remote server. In one example, a client device 1202 can be mobile. In another example, a client device 1202 can be stationary. According to one aspect of the disclosure, a client device 1202 may be a device having at least a processor and memory, where the total amount of memory of the client device 1202 could be less than the total amount of memory in a server 1206. In one example, a client device 1202 does not have a hard disk. In one aspect, a client device 1202 has a display smaller than a display supported by a server 1206. In one aspect, a client device may include one or more client devices.

In some embodiments, a server 1206 may represent a computer, a laptop computer, a computing device, a virtual machine (e.g., VMware® Virtual Machine), a desktop session (e.g., Microsoft Terminal Server), a published application (e.g., Microsoft Terminal Server) or a suitable device with a processor. In some embodiments, a server 1206 can be stationary. In some embodiments, a server 1206 can be mobile. In certain configurations, a server 1206 may be any device that can represent a client device. In some embodiments, a server 1206 may include one or more servers.

In one example, a first device is remote to a second device when the first device is not directly connected to the second device. In one example, a first remote device may be connected to a second device over a communication network such as a Local Area Network (LAN), a Wide Area Network (WAN), and/or other network.

When a client device 1202 and a server 1206 are remote with respect to each other, a client device 1202 may connect to a server 1206 over a network 1204, for example, via a modem connection, a LAN connection including the Ethernet or a broadband WAN connection including DSL, Cable, T1, T3, Fiber Optics, Wi-Fi, or a mobile network connection including GSM, GPRS, 3G, WiMax or other network connection. A network 1204 can be a LAN network, a WAN network, a wireless network, the Internet, an intranet or other network. A network 1204 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name or other system name. These illustrate some examples as to how one device may be remote to another device. But the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or vice versa.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A system for evaluating patient treatment options, comprising:
    memory,
    one or more processors coupled to the memory, the one or more processors configured to execute a plurality of modules including:
    an ordinal ranking module configured to display a set of relative-weighting queries regarding a relative importance of at least two criteria to a treatment goal, receive one or more relative-weighting indicator responses to the set of relative-weighting queries, and modify a set of criteria weights based on the one or more relative-weighting indicator responses;
    a direct weighting module configured to display a set of direct-weighting queries regarding an individual importance of at least one criterion to the treatment goal, receive one or more direct-weighting indicator responses to the set of direct-weighting queries, and modify the set of criteria weights based on the one or more direct-weighting indicator responses;
    an analysis module configured to display a set of analytic queries comparing the at least two criteria, receive one or more analytic indicator responses to the set of analytic queries, and modify the set of criteria weights based on the one or more analytic indicator responses;
    wherein at least one of the plurality of modules is configured to retrieve data descriptive of a plurality of treatment options at least with respect to the at least two criteria;
    wherein at least one of the plurality of modules is configured to display a set of criterion-exclusion queries, and receive one or more criterion-exclusion indicator responses to the set of criterion-inclusion queries;
    wherein at least one of the plurality of modules is configured to calculate, based on at least a portion of the data and the set of criteria weights, and display a composite score for each treatment option except as indicated by the one or more criterion-exclusion indicator responses; and
    wherein at least one of the plurality of modules is configured to determine whether at least one response is inconsistent with another received response, and, in response to determining existence of an inconsistency, to perform at least one of: (a) displaying a notice regarding the inconsistency, (b) displaying a resolution query directed to resolution of the inconsistency, (c) identifying at least one objectively incorrect understanding of a user indicated by the inconsistency and displaying information directed to correction of the at least one objectively incorrect understanding, or (d) notifying a health care provider of the inconsistency.

2. The system of claim 1, further comprising a balance sheet module configured to display at least a portion of the data in a table according to criteria and treatment options.

3. The system of claim 1, further comprising a decision dashboard module configured to display a graphical representation of a least a portion of the data.

4. The system of claim 1, further comprising a decision strategy module configured to receive decision information including the at least two criteria and the plurality of treatment options.

5. The system of claim 1, wherein the analysis module is further configured to provide information related to consistency of analytic indicator responses.

6. The system of claim 1, further comprising a sensitivity analysis module configured to examine effects of variation of the set of criteria weights.

7. The system of claim 1, wherein the at least two criteria include effectiveness, risk of side effects, and cost of a treatment strategy.

8. The system of claim 1, wherein at least some of the analytic queries in the set compare only two of the at least two criteria.

9. The system of claim 1, wherein the analysis module is further configured to display a set of preference queries comparing attributes, relative to one of the at least two criteria, of at least two treatment options, receive one or more preference indicator responses to the set of preference queries, and modify the set of criteria weights based on the one or more preference indicator responses.

10. A method for evaluating patient treatment options, comprising:
    a) retrieving, from a non-transitory machine-readable medium, data indicative of attributes of a plurality of treatment options relative to criteria;

b) displaying a set of criterion-exclusion queries and receiving one or more criterion-exclusion indicator responses to the set of criterion-inclusion queries;
c) displaying a set of relative-weighting queries regarding a relative importance of at least two criteria to a treatment goal, receiving one or more relative-weighting indicator responses to the set of relative-weighting queries, and modifying a set of criteria weights based on the one or more relative-weighting indicator responses;
d) displaying a set of direct-weighting queries regarding an individual importance of at least one criterion to the treatment goal, receiving one or more direct-weighting indicator responses to the set of direct-weighting queries, and modifying the set of criteria weights based on the one or more direct-weighting indicator responses;
e) displaying a set of analytic queries comparing the at least two criteria, receiving one or more analytic indicator responses to the set of analytic queries, and modifying the set of criteria weights based on the one or more analytic indicator responses;
f) repeating at least one of steps b, c, d, or e;
g) by a processor, determining whether at least one response is inconsistent with another received response, and, in response to determining existence of an inconsistency, performing at least one of: (i) displaying a notice regarding the inconsistency, (ii) displaying a resolution query directed to resolution of the inconsistency, (iii) identifying at least one objectively incorrect understanding of a user indicated by the inconsistency and displaying information directed to correction of the at least one objectively incorrect understanding, or (iv) notifying a health care provider of the inconsistency; and
h) calculating, based on at least a portion of the data and the set of criteria weights, and displaying a composite score for each treatment option except those indicated by the one or more criterion-exclusion indicator responses.

11. The method of claim 10, further comprising alphanumerically displaying the data.

12. The method of claim 10, further comprising graphically displaying at least a portion of the data.

13. The method of claim 10, further comprising displaying an option-selection query and receiving a selection indicator response to the option-selection query.

14. A method for evaluating patient treatment options, comprising:
a) displaying, by a first processor, information regarding (1) a plurality of treatment options and (2) one or more of (i) a set of criterion-exclusion queries, (ii) a set of relative-weighting queries regarding a relative importance of at least two criteria to a treatment goal, (iii) a set of direct-weighting queries regarding an individual importance of at least one criterion to the treatment goal, or (iv) a set of analytic queries comparing at least two criteria;
b) receiving one or more indicator responses to the displayed queries;
c) storing, in a non-transitory machine-readable medium, at least one of (i) the received one or more indicator responses or (ii) a set of criteria weights determined based on the received one or more indicator responses;
d) calculating a composite score for an additional treatment option, not comprised by the plurality of treatment options, based on (1) data indicative of attributes of the additional treatment option relative to the at least two criteria, and (2) at least a portion of the stored one of (i) the received one or more indicator responses or (ii) the set of criteria weights; and
e) outputting an indicator of the composite score.

15. The method of claim 14, wherein the indicator of the composite score comprises an indication of potential preference for the additional treatment option over at least one other treatment option.

16. The method of claim 14, wherein the indicator of the composite score comprises an indication that the composite score of the additional treatment option is better than composite scores of each of a plurality of treatment options.

17. The method of claim 14, wherein outputting the indicator of the composite score comprises displaying the composite score.

18. The method of claim 14, further comprising calculating a composite score for each of the plurality of treatment options based on (1) data indicative of attributes of the plurality of treatment options relative to the at least two criteria, and (2) at least a portion of one of (i) the received one or more indicator responses or (ii) the set of criteria weights; and displaying the composite scores for the plurality of treatment options.

19. The method of claim 18, wherein the composite scores for the plurality of treatment options are calculated based on the stored one of (i) the received one or more indicator responses or (ii) the set of criteria weights.

20. The method of claim 14, wherein the additional treatment option was not displayed to a user prior to storing the at least one of (i) the received one or more indicator responses or (ii) the set of criteria weights, wherein the received one or more indicator responses were received from the user.

* * * * *